US009146243B2

(12) United States Patent
Stoll et al.

(10) Patent No.: US 9,146,243 B2
(45) Date of Patent: Sep. 29, 2015

(54) METHOD OF ASSESSING DIABETIC NEPHROPATHY USING CD5 ANTIGEN-LIKE

(71) Applicants: PROTEOMICS INTERNATIONAL PTY LTD, Crawley, Western Australia (AU); THE UNIVERSITY OF WESTERN AUSTRALIA, Crawley, Western Australia (AU)

(72) Inventors: Thomas Stoll, Windorf (DE); Scott Bringans, Harrisdale (AU); Kaye Winfield, Bayswater (AU); Tammy Casey, Mount Pleasant (AU); Wendy Davis, Cottesloe (AU); Kirsten Peters, Wellard (AU); Timothy Davis, Cottesloe (AU); Richard Lipscombe, Floreat (AU)

(73) Assignees: Proteomics International Pty Ltd, Crawley (AU); The University of Western Australia, Crawley (AU)

( * ) Notice: Subject to any disclaimer, the term of this patent is extended or adjusted under 35 U.S.C. 154(b) by 0 days.

(21) Appl. No.: 14/277,371

(22) Filed: May 14, 2014

(65) Prior Publication Data

US 2014/0249049 A1    Sep. 4, 2014

Related U.S. Application Data

(63) Continuation of application No. 13/824,359, filed as application No. PCT/AU2011/001212 on Sep. 20, 2011, now abandoned.

(30) Foreign Application Priority Data

Sep. 21, 2010  (AU) ................................ 2010904249

(51) Int. Cl.
C12Q 1/37    (2006.01)
G01N 33/68   (2006.01)
C12Q 1/68    (2006.01)

(52) U.S. Cl.
CPC .......... *G01N 33/6893* (2013.01); *C12Q 1/6883* (2013.01); *G01N 33/6848* (2013.01); *C12Q 2600/158* (2013.01); *G01N 2333/4716* (2013.01); *G01N 2333/775* (2013.01); *G01N 2333/908* (2013.01); *G01N 2333/90212* (2013.01); *G01N 2800/042* (2013.01); *G01N 2800/347* (2013.01); *G01N 2800/50* (2013.01)

(58) Field of Classification Search
IPC .................................... C12Q 1/37; G01N 30/72
See application file for complete search history.

(56) References Cited

U.S. PATENT DOCUMENTS

| 2010/0136540 | A1 | 6/2010 | Hamet et al. | |
| 2011/0311650 | A1 | 12/2011 | Wang et al. | |
| 2012/0309040 | A1* | 12/2012 | Madian et al. | .................. 435/23 |

FOREIGN PATENT DOCUMENTS

| KR | 100792630 | 1/2008 |
| WO | 2007028636 | 3/2007 |

OTHER PUBLICATIONS

International Search Report for PCT/AU2011/001212, Completed by the Australian Patent Office on Dec. 14, 2011, 8 Pages.
Granier et al. Nephrol. Dial Transplant 2008, vol. 23, p. 792-799, "Gene and protein markers of diabetic nephropathy."
Bostrom et al. Diabetes Feb. 2009, vol. 58, p. 499-504, "Association of Adiponectin Gene Polymorphisms With Type 2 Diabetes in an African American Population Enriched for Nephropathy."
Rao et al. Diabetes Care Mar. 2007, vol. 30, No. 3, p. 629-637, "Proteomic Identiciation of Urinary Biomarkers of Diabetic Nephropathy."
Altschul et al. J. Mol. Biol. 1990 vol. 215, p. 403-410, "Basic Local Alignment Search Tool."
Devereux et al. Nucleic Acids Research 1984, vol. 12, No. 1, p. 387-395, "A comprehensive set of sequence analysis programs for the VAX."
Kim et al. Journal of Proteome Research 2010, vol. 9, p. 689-699, Published on Web Dec. 18, 2009, "Verification of Biomarkers for Diabetic Retinopathy by Multiple Reaction Monitoring."
Komura et al. Cardiovascular Research 2010, vol. 86, p. 471-477, "Increment and impairment of adiponectin in renal failure."
Rao et al. Journal of Proteome Research 2009, vol. 8, p. 239-245, Published on Web Jan. 2, 2009, "Proteomic Identification of Salivary Biomarkers of Type-2 Diabetes."
Salomaa et al. PLoS One Apr. 2010, vol. 5, Issue 4, p. 1-8, "Thirty-One Novel Biomarkers as Predictors for Clinically Incident Diabetes."
Saraheimo et al. Diabetes Care Jun. 2008, vol. 31, No. 6, p. 1165-1169, "Serum Adiponectin and Progression of Diabetic Nephropathy in Patients With Type 1 Diabetes."
Vasylyeva et al. Diabetes Res. Clin. Pract. May 2007, vol. 76, No. 2, p. 177-186, "Novel roles of the IGF-IGFBP axis in etiopathophysiology of diabetic nephropathy."
Wu et al. Nephrol Dialysis Transplantation Jun. 8, 2009, p. 1-7, "Association and interaction analyses of genetic variants in ADIPOQ, ENPP1, GHSR, PPARγ and TCF7L2 genes for diabetic nephropathy in a Taiwanese population with type 2 diabetes."
Proteomics International Sep. 29, 2010, 1 Page, "Discovery and validation of 13 diabetes biomarkers to be commercialized."
Long et al. Bulletin of Hunan Medical University 1995, vol. 20, 1 Page English Abstract, "Analysis of serum apolipoprotein profile in middle-aged and old-aged patients with diabetic nephropathy."

* cited by examiner

*Primary Examiner* — Ralph Gitomer
(74) *Attorney, Agent, or Firm* — Suzannah K. Sundby, Esq.; Canady + Lortz LLP

(57) ABSTRACT

Biomarkers for pre-Diabetes, Diabetes and/or a Diabetes related conditions, and methods of their use, including the biomarkers in Tables 1 and 2 such as peroxiredoxin-2, complement C1q subcomponent subunit B, sulfhydryl oxidase 1 and apolipoprotein A-IV.

15 Claims, 5 Drawing Sheets

Figure 1

| Study | Name | Accession number | State change | Fold difference | p value (Mann-Whitney) |
|---|---|---|---|---|---|
| FDS1 | Peroxiredoxin-2 | P32119 | up | 2.3 | 0.01 |
| | Protein AMBP | P02760 | up | 1.3 | 0.01 |
| | Apolipoprotein A-IV | P06727 | up | 2 | 0.05 |
| FDS2 | Complement C1q subcomponent subunit B | P02746 | down | 3 | 0.0016 |
| | Apolipoprotein A-IV | P06727 | up | 1.5 | 0.08 |
| | Apolipoprotein C-III | P02656 | up | 2.3 | 0.056 |
| | Insulin-like growth factor- | P17936 | down | 1.7 | 0.07 |
| | Protein AMBP | P02760 | down | 1.3 | 0.037 |
| | Adiponectin | Q15848 | down | 2 | 0.04 |
| | Complement factor H-related protein 2 | P36980 | down | 1.7 | 0.03 |
| | Haemoglobin subunit beta | P68871 | up | 3.5 | 0.05 |
| BDS | CD5 antigen-like | O43866 | down | 2 | 0.06 |
| | Apolipoprotein B-100 | P04114 | up | 1.3 | 0.045 |

Figure 5

| Study | Name | Accession number | State change | Fold difference | p value (Mann-Whitney) |
|---|---|---|---|---|---|
| BDS | Sulfhydryl oxidase 1 | O00391 | up | 1.7 | 0.045 |
| | Apolipoprotein A-IV | P06727 | up | 1.7 | 0.05 |
| | Complement component C8 beta chain | P07358 | up | 1.3 | 0.09 |

SEQUENCE LISTING

```
<160> NUMBER OF SEQ ID NOS: 20

<210> SEQ ID NO 1
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 1

Ser Phe Tyr Thr Ala Tyr Leu Gln Arg
1               5

<210> SEQ ID NO 2
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 2

Leu Glu Pro Tyr Ala Asp Gln Leu Arg
1               5

<210> SEQ ID NO 3
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 3

Ile Ser Ala Ser Ala Glu Glu Leu Arg
1               5

<210> SEQ ID NO 4
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 4

Leu Val Gly Gly Asp Asn Leu Cys Ser Gly
1               5                   10

<210> SEQ ID NO 5
```

```
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 5

Ile Trp Leu Asp Asn Val Arg
1               5

<210> SEQ ID NO 6
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 6

Cys Glu Gly Phe Val Cys Ala Gln Thr Gly Arg
1               5                   10

<210> SEQ ID NO 7
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 7

Ser Val Ser Leu Pro Ser Leu Asp Pro Ala Ser Ala Lys
1               5                   10

<210> SEQ ID NO 8
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 8

Thr Glu Val Ile Pro Pro Leu Ile Glu Asn Arg
1               5                   10

<210> SEQ ID NO 9
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 9

Ala Thr Ala Val Val Asp Gly Ala Phe Lys
1               5                   10
```

```
<210> SEQ ID NO 10
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 10

Thr Val Ala Ala Cys Asn Leu Pro Ile Val Arg
1               5                   10

<210> SEQ ID NO 11
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 11

Glu Tyr Cys Gly Val Pro Gly Asp Gly Asp Glu Glu Leu Leu Arg
1               5                   10                  15

<210> SEQ ID NO 12
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 12

Ser Ala Val Thr Ala Leu Trp Gly Lys
1               5

<210> SEQ ID NO 13
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 13

Val Asn Val Asp Glu Val Gly Gly Glu Ala Leu Gly Arg
1               5                   10

<210> SEQ ID NO 14
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 14

Ile Ala Phe Ser Ala Thr Arg
1               5
```

<210> SEQ ID NO 15
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"

<400> SEQUENCE: 15

Asp Ala Leu Ser Ser Val Gln Glu Ser Gln Val Ala Gln Gln Ala Arg
1               5                   10                  15

<210> SEQ ID NO 16
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 16

Ala Leu Ala Gln Cys Ala Pro Pro Ala Val Cys Ala Glu Leu Val
1               5                   10                  15

Arg Arg

<210> SEQ ID NO 17
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 17

Phe Leu Asn Val Leu Ser Pro Arg
1               5

<210> SEQ ID NO 18
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 18

Gly Asp Ile Gly Glu Thr Gly Val Pro Gly Ala Glu Gly Pro Arg
1               5                   10                  15

<210> SEQ ID NO 19
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 19

-continued

```
Thr Gly Asp Ile Val Glu Phe Val Cys Lys
1               5                   10

<210> SEQ ID NO 20
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 20

Leu Val Tyr Pro Ser Cys Glu Glu Lys
1               5
```

METHOD OF ASSESSING DIABETIC NEPHROPATHY USING CD5 ANTIGEN-LIKE

CROSS-REFERENCE TO RELATED APPLICATION

This application is a continuation of Ser. No. 13/824,359 filed Mar. 16, 2013, now abandoned, which is a National Stage application filed under Rule 371 based upon PCT/AU2011/001212 filed Sep. 20, 2011.

SEQUENCE LISTING

The text file is Sequence Listing pctau2011001212-seq1.txt, created Mar. 16, 2013, and of size 6 KB, filed therewith, is hereby incorporated by reference.

FIELD OF THE INVENTION

The invention relates to biomarkers associated with pre-Diabetes, Diabetes and Diabetes related conditions, such as diabetic nephropathy, methods of using the biomarkers to determine the risk that an individual will develop pre-Diabetes, Diabetes and Diabetes related conditions, methods of screening a population to identify persons at risk for developing pre-Diabetes, Diabetes and Diabetes related conditions and drug targets for pre-Diabetes, Diabetes and Diabetes.

BACKGROUND TO THE INVENTION

Diabetes mellitus is a chronic disease and one of the major public health problems of our time. Worldwide there is an ever increasing population of patients with diabetes that are imposing a major financial burden on health systems. The prevalence of diabetes for all age-groups worldwide was estimated to be 2.8% in 2000 and 4.4% by 2030. The total number of people with diabetes is projected to rise from 171 million in 2000 to 366 million in 2030. In 2002 the prevalence of diabetes in the Australian population was 7.4% in those 25 years and older, and the number of Australians with diabetes has trebled since 1981.

Type 2 diabetes is by far the most common, e.g. affecting 90 to 95% of the U.S. diabetes population. Diabetes mellitus prevalence increases with age, and the numbers of older persons with diabetes are expected to grow as the elderly population increases in number. Along with the rising rate of diabetes there is also a higher prevalence of impaired glucose metabolism, which is associated with an increased risk of heart disease and diabetes. Diabesity is a term which encompasses the prevalence of diabetes, obesity, impaired glucose metabolism and the associated risk factors of hypertension and abnormal plasma lipid profiles (dyslipideamia). The "diabetes epidemic" will continue even if levels of obesity remain constant. Given the increasing prevalence of obesity, it is likely that these figures underestimate future diabetes prevalence.

Diabetes mellitus is a condition where the body cannot maintain normal blood glucose levels. Most cases of diabetes mellitus fall into three broad categories: Type 1, Type 2 and gestational diabetes. Type 1 diabetes results from the body's failure to produce insulin, and presently requires the person to inject insulin. Type 2 diabetes results from insulin resistance, a condition in which cells fail to use insulin properly, sometimes combined with an absolute insulin deficiency.

Type 2 diabetes can usually be controlled in the first instance by regular exercise and diet. Tablets and eventually insulin injections may be needed as the disease progresses.

Over time, high blood glucose levels may damage blood vessels and nerves. These complications of diabetes can cause damage to eyes, nerves and kidneys and increase the risk of heart attack, stroke, impotence and foot problems. This damage can happen before an individual knows that they have diabetes if left undetected for a long time. Therefore, it is important to diagnose and control diabetes and its complications at a very early stage.

Diabetes is also the largest cause of kidney disease (nephropathy) in developed countries and is accountable for huge costs in dialysis. 10% to 20% of people with diabetes will die of kidney (renal) failure. The reasons behind the complication of nephropathy in diabetes is complex, and includes the toxic effects of high glucose levels; elevated blood pressure; abnormal lipid levels and abnormalities of small blood vessels. The accumulative result is that there is thickening of the glomeruli in the kidney which allows protein (albumin) to be excreted in the urine.

Diabetes has become the single most common cause of end stage renal failure (ESRF) at 40-50% of ESRD cases and annual Australian Medicare expenditures are greatest for patients with ESRF caused by diabetes compared with all other primary ESRD diagnoses. Up to one-third of adults with newly diagnosed type 2 diabetes already have chronic renal disease, and data suggest that in many of these patients it may have developed in the course of the pre-diabetic state. The disease is progressive and affects more men than women.

Diabetic nephropathy is detected primarily by measuring the amount of albumin excreted in the urine (albuminuria). Albuminuria is usually measured using the albumin creatinine ratio (ACR). This is the ratio between the albumin and the creatinine in the urine. The ratio considers the concentration of the albumin in relation to the glomerular filtration rate, which is determined by the amount of creatinine in the urine. Albuminuria is defined as: ACR>2.5 mg/mmol (men) or >3.5 mg/mmol (women).

Despite numerous studies and algorithms that have been used to assess the risk of Diabetes and related conditions, there remains a need for accurate methods of assessing such risks or conditions that can be readily adopted by primary care physicians who are most likely to initially encounter the pre-diabetic or undiagnosed early diabetic.

Accordingly, there remains a need for relatively inexpensive and convenient methods for screening persons at risk for developing pre-Diabetes, Diabetes and/or a Diabetes related condition and for monitoring patients with pre-Diabetes, Diabetes and/or a Diabetes related condition. Such methods could be used for screening a large population to identify persons at risk for Diabetes, for testing a single person to determine that individual's risk of developing Diabetes, for monitoring the health of diabetes patients and assessing the efficacy of interventions designed to treat Diabetes, pre-Diabetes and/or related conditions. There is also a need to identify new drug targets for pre-Diabetes, Diabetes and/or Diabetes related conditions including protein drug targets. Identification of new drug targets will enable the development of new interventions for pre-Diabetes, Diabetes and/or Diabetes related conditions.

It is against this background and the problems and difficulties associated therewith that the present invention has been developed.

SUMMARY OF THE INVENTION

In one aspect, the present invention provides a method of assessing a subject for pre-Diabetes, Diabetes and/or a Diabetes related condition comprising measuring at least one biomarker in a sample from the subject, wherein said at least one biomarker is selected from the list of biomarkers in Table 1 or 2.

TABLE 1

| Protein | Accession number (UniProt Database) |
| --- | --- |
| Peroxiredoxin-2 | P32119 |
| Protein AMBP | P02760 |
| Complement C1q subcomponent subunit | P02746 |
| Apolipoprotein A-IV | P06727 |
| Apolipoprotein C-III | P02656 |
| Insulin-like growth factor-binding protein | P17936 |
| Adiponectin | Q15848 |
| Complement factor H-related protein 2 | P36980 |
| Haemoglobin subunit beta | P68871 |
| CD5 antigen-like | O43866 |
| Apolipoprotein B-100 | P04114 |
| Sulfhydryl oxidase 1 | O00391 |
| Complement component C8 beta chain | P07358 |

TABLE 2

| Protein | Accession number (UniProt Database) |
| --- | --- |
| Peroxiredoxin-2 | P32119 |
| Protein AMBP | P02760 |
| Complement C1q subcomponent subunit B | P02746 |
| Adiponectin | Q15848 |
| Complement factor H-related protein 2 | P36980 |
| Apolipoprotein B-100 | P04114 |
| Sulfhydryl oxidase 1 | O00391 |
| Apolipoprotein A-IV | P06727 |

In another aspect the present invention provides a kit comprising reagents for measuring at least one biomarker in a sample from a subject, wherein said at least one biomarker is selected from the list of biomarkers in Table 1 or 2.

In another aspect the present invention provides a computer readable medium having computer executable instructions for assessing a subject for pre-Diabetes, Diabetes and/or a Diabetes related condition, the computer readable medium comprising: a routine, stored on the computer readable medium and adapted to be executed by a processor, to store biomarker measurement data representing at least one biomarker selected from the list of biomarkers in Table 1 or 2.

In another aspect the present invention provides a method of assessing a treatment for pre-Diabetes, Diabetes and/or a Diabetes related condition in a subject comprising measuring at least one biomarker, in a sample from the subject undergoing the treatment, selected from the list of biomarkers in Table 1 or 2, at least twice over the course of the treatment.

In another aspect the present invention provides a method of assessing the risk of a subject developing pre-Diabetes, Diabetes and/or a Diabetes related condition comprising measuring at least one biomarker, in a sample from the subject, selected from the list of biomarkers in Table 1 or 2.

In another aspect the present invention provides a method of monitoring pre-Diabetes, Diabetes and/or a Diabetes related condition in a subject comprising measuring at least one biomarker, in a sample from the subject, selected from the list of biomarkers in Table 1 or 2 and comparing the measurement obtained with another measure of the at least one biomarker.

In another aspect the present invention provides a method of diagnosing or identifying pre-Diabetes, Diabetes and/or a Diabetes related condition in a subject comprising measuring at least one biomarker, in a sample from the subject, selected from the list of biomarkers in Table 1 or 2.

In another aspect the present invention provides a method of differentially diagnosing kidney disease from other conditions that also cause proteinuria in a subject comprising measuring at least one biomarker, in a sample from the subject, selected from the list of biomarkers in Table 1 or 2.

In another aspect the present invention provides a method of differentially diagnosing sub-classes or stages of pre-Diabetes, Diabetes and/or a Diabetes related condition in a subject comprising measuring at least one biomarker, in a sample from the subject, selected from the list of biomarkers in Table 1 or 2.

In another aspect the present invention provides a test system comprising:
 (i) means for obtaining test results data representing levels of at least one biomarker selected from the list of biomarkers in Table 1 or 2, in a sample from the subject;
 (ii) means for collecting and tracking the test results data generated in step (i);
 (iii) means for calculating a pre-Diabetes, Diabetes and/or a Diabetes related condition risk index value from the test results data, wherein said risk index value is representative of the risk of an individual developing or having pre-Diabetes, Diabetes and/or a Diabetes related condition; and
 (iv) means for reporting said risk index value.

In another aspect the present invention provides a method of ranking or grouping a population of individuals, comprising: obtaining pre-Diabetes, Diabetes and/or a Diabetes related condition risk index data for individuals in said population; and ranking individuals within the population relative to the remaining individuals in the population or dividing the population into at least two groups, based on factors comprising said obtained risk index data.

In another aspect the present invention provides a method of evaluating a pre-Diabetes, Diabetes and/or a Diabetes related condition surrogate endpoint in a subject, the method comprising: measuring at least one biomarker from the list of biomarkers in Table 1 or 2; and evaluating a pre-Diabetes, Diabetes and/or a Diabetes related condition surrogate endpoint in the subject based on said measure.

In another aspect the present invention provides a method of evaluating the risk of a subject developing pre-Diabetes, Diabetes and/or a Diabetes related condition comprising measuring at least one biomarker in a sample from the subject, wherein said at least one biomarker is selected from the list of biomarkers in Table 1 or 2.

In another aspect the present invention provides a method of monitoring the risk of a subject developing pre-Diabetes, Diabetes and/or a Diabetes related condition comprising measuring at least one biomarker in a sample from the subject, wherein said at least one biomarker is selected from the list of biomarkers in Table 1 or 2.

In another aspect the present invention provides a method of diagnosing or identifying a subject with pre-Diabetes, Diabetes and/or a Diabetes related condition comprising measuring at least one biomarker in a sample from the subject, wherein said at least one biomarker is selected from the list of biomarkers in Table 1 or 2.

In another aspect the present invention provides a method of monitoring pre-Diabetes, Diabetes and/or a Diabetes related condition therapy or intervention comprising measuring at least one biomarker in a sample from the subject, wherein said at least one biomarker is selected from the list of biomarkers in Table 1 or 2.

In another aspect the present invention provides a method of differentially diagnosing a disease state or sub-class of pre-Diabetes, Diabetes and/or a Diabetes related condition comprising measuring at least one biomarker in a sample from the subject, wherein said at least one biomarker is selected from the list of biomarkers in Table 1 or 2.

In another aspect the present invention provides a method of treating pre-Diabetes, Diabetes and/or a Diabetes related condition in a subject comprising: evaluating risk, for the subject, of developing pre-Diabetes, Diabetes and/or a Diabetes related condition using at least one biomarker from Table 1 or 2 and treating the subject when identified as being at elevated risk for pre-Diabetes, Diabetes and/or a Diabetes related condition with a treatment regimen to delay or prevent the onset of pre-Diabetes, Diabetes and/or a Diabetes related condition.

In another aspect the present invention provides a method of ranking or grouping a population of subjects, comprising: obtaining data representing a pre-Diabetes, Diabetes and/or a Diabetes related condition risk score for subjects comprised within said population, wherein said risk score is calculated using at least one biomarker from Table 1 or 2 and ranking subjects within the population relative to the remaining individuals in the population or dividing the population into at least two groups, based on factors comprising said obtained risk score data.

In another aspect the present invention provides a method of identifying or assessing an agent for treating or reducing the risk of developing pre-Diabetes, Diabetes and/or a Diabetes related condition comprising:
(i) contacting cells expressing at least one biomarker from Table 1 or 2 with a putative agent; and
(ii) comparing expression and/or levels of at least one biomarker from Table 1 in the cells prior to contact with the putative agent to expression and/or levels of at least one biomarker from Table 1 or 2 in the cells after contact with the putative agent;
wherein a change in the level or expression identifies the agent as an agent for treating pre-Diabetes, Diabetes and/or a Diabetes related condition.

Thus, another aspect of the present invention provides for the use of at least one biomarker in Table 1 or 2 as a drug target for pre-Diabetes, Diabetes and/or a Diabetes related condition.

In another aspect the present invention provides a method of treating or reducing the risk of developing pre-Diabetes, Diabetes and/or a Diabetes related condition in a subject comprising administering to the subject an effective amount of an agent adapted to change the expression or level of at least one biomarker in Table 1 or 2.

In another aspect the present invention provides for the use of an agent adapted to change the expression or level of at least one biomarker in Table 1 or 2 for preparing a medication for treating or reducing the risk of developing pre-Diabetes, Diabetes and/or a Diabetes related condition.

BRIEF DESCRIPTION OF DRAWINGS

The following Detailed Description of the Invention, given by way of example, but not intended to limit the invention to specific embodiments described, may be understood in conjunction with the accompanying Figures, in which:

FIG. 1 is a table listing biomarker protein data obtained from three studies with respect to the presence of diabetic nephropathy in diabetes patients measured by multiple reaction monitoring (MRM);

FIG. 5 is a table listing biomarker protein data obtained from the BDS study with respect to patients with diabetic nephropathy and healthy patients measured by MRM.

DETAILED DESCRIPTION OF THE INVENTION

Figure 2:
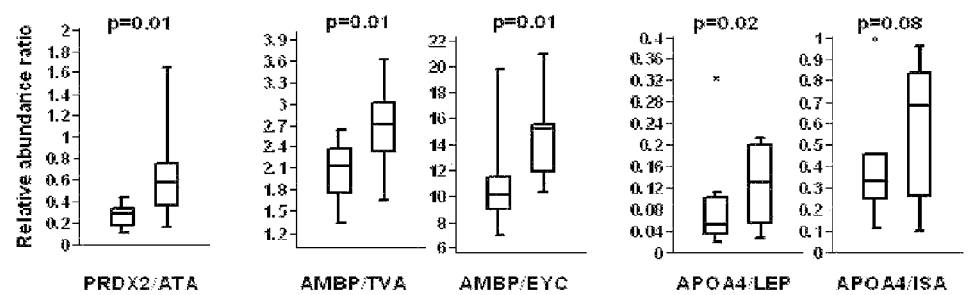
FIG. 2 is a series of box-whisker plots for each biomarker listed in FIG. 1 from the FDS1 study (left boxplot: diabetic group; right boxplot: diabetic group with severe nephropathy; x-axis: protein/peptide; y-axis: Relative abundance ratio; peptide sequences: ATA=ATAVVDGAFK; TVA=TVAACNLPIVR; EYC=EYCGVPGDGDEELLR; LEP=LEPYADQLR; and ISA=ISASAEELR)

The present invention relates to the identification of biomarkers associated with pre-Diabetes, Diabetes and/or Diabetes related conditions, such as diabetic nephropathy. Accordingly, the present invention features methods for identifying subjects who are at risk of developing pre-Diabetes, Diabetes and/or Diabetes related conditions, including those subjects who are asymptomatic or only exhibit non-specific indicators of pre-Diabetes, Diabetes and/or Diabetes related conditions by detection of the biomarkers disclosed herein. These biomarkers are also useful for monitoring subjects undergoing treatments and therapies for pre-Diabetes, Diabetes and/or Diabetes related conditions, and for selecting or modifying therapies and treatments that would be efficacious in subjects having pre-Diabetes, Diabetes and/or Diabetes related conditions, wherein selection and use of such treatments and therapies slow the progression of pre-Diabetes, Diabetes and/or Diabetes related conditions, or prevent their onset. The present invention also features new drug targets for pre-Diabetes, Diabetes and/or Diabetes related conditions comprising at least one of the biomarkers in Table 1 or 2.

DEFINITIONS

"Agents for treating or reducing the risk of developing pre-Diabetes, Diabetes and/or a Diabetes related condition" include: insulin such as mature insulin, pro-insulin and soluble c-peptide (SCp), rapid acting forms of insulin, regular insulin, intermediate-acting insulin and long-acting forms of insulin; hypoglycaemic agents; anti-inflammatory agents; lipid reducing agents; anti-hypertensives such as calcium channel blockers, beta-adrenergic receptor blockers, cyclooxygenase-2 inhibitors including prodrugs of COX-2 inhibitors, angiotensin system inhibitors including angiotensin II receptor blockers (ARBs), ACE inhibitors and renin inhibitors including amino acids and derivatives thereof, peptides and derivatives thereof, and antibodies to renin.

"Angiotensin II antagonists" are compounds which interfere with the activity of angiotensin II by binding to angiotensin II receptors and interfering with its activity and include peptide compounds and non-peptide compounds. Most angiotensin II antagonists are slightly modified congeners in which agonist activity is attenuated by replacement of phenylalanine in position 8 with some other amino acid. Examples of angiotensin II antagonists include: peptidic compounds (e.g., saralasin, angiotensin-(1-8) octapeptide and related analogs); N-substituted imidazole-2-one; imidazole acetate derivatives including 2-N-butyl-4-chloro-1-(2-chlorobenzile) imidazole-5-acetic acid; 4,5,6,7-tetrahydro-1H-imidazo[4,5-c]pyridine-6-carboxylic acid and analog derivatives; N2-tetrazole beta-glucuronide analogs; substituted pyrroles, pyrazoles, and tryazoles; phenol and heterocyclic derivatives such as 1,3-imidazoles; imidazo-fused 7-member ring heterocycles; antibodies to angiotensin II; and aralkyl imidazole compounds such as biphenyl-methyl substituted imidazoles; ES8891 (N-morpholinoacetyl-(-1-naphthyl)-L-alany-1-(4, thiazolyl)-L-alanyl (35,45)-4-amino-3-hydroxy-5-cyclo-hexapentanoyl-N-hexylamide); SKF108566 (E-alpha-2-[2-butyl-1-(carboxy phenyl)methyl] 1H-imidazole-5-yl[methylan-e]-2-thiophenepropanoic acid); Losartan (DUP753/MK954); and Remikirin.

"Angiotensin converting enzyme (ACE) inhibitors" include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. Classes of compounds known to be useful as ACE inhibitors include acylmercapto and mercaptoalkanoyl prolines such as captopril and zofenopril, carboxyalkyl dipeptides such as enalapril, lisinopril, quinapril, ramipril, and perindopril, carboxyalkyl dipeptide mimics such as cilazapril and benazapril, phosphinylalkanoyl prolines such as fosinopril and trandolopril.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium, aspirin, cytokine inhibitors such as cytokine antagonists (e.g., IL-6 receptor antagonists), aza-alkyl lysophospholipids (AALP), and Tumor Necrosis Factor-alpha (TNF-alpha) inhibitors, such as anti-TNF-alpha antibodies, soluble TNF receptor, TNF-alpha, anti-sense nucleic acid molecules, multivalent guanylhydrazone (CNI-1493), N-acetylcysteine, pentoxiphylline, oxpentifylline, carbocyclic nucleoside analogues, Dexanabinol and TNF-alpha inhibitors such as Etanercept and Infliximab.

"Beta-adrenergic receptor blocking agents" antagonize the cardiovascular effects of catecholamines in angina pectoris, hypertension, and cardiac arrhythmias and include atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl—, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxypropylthio)-4-(5-carbamoyl-2-thienyl)thiazole and 7-(2-hydroxy-3-t-butylaminpropoxy) phthalide.

"Calcium channel blockers" belong to one of three major chemical groups of drugs, the dihydropyridines, such as nifedipine, the phenyl alkyl amines, such as verapamil, and the benzothiazepines, such as diltiazem. Other calcium channel blockers useful according to the invention include aminone, amlodipine, bencyclane, felodipine, fendiline, flunarizine, isradipine, nicardipine, nimodipine, perhexylene, gallopamil, tiapamil and tiapamil analogues, phenyloin, barbiturates, and the peptides dynorphin, omega-conotoxin, and omega-agatoxin.

"Diabetes" includes Type 1 Diabetes, both autoimmune and idiopathic, Type 2 Diabetes and gestational Diabetes. Diabetes can be characterised by recurrent and persistent hyperglycaemia and may be diagnosed by increased blood glucose levels and glycated haemoglobin (≥6.5%). According to the current definition, two fasting glucose measurements above 126 mg/dL (7.0 mmol/L) is considered diagnostic for Diabetes Mellitus.

"Diabetes related condition" includes any condition or disease that is a result or complication of or is otherwise correlated or associated with Diabetes including a condition caused by higher than normal blood glucose levels and a condition selected from the list consisting of: hypoglycaemia, diabetic ketoacidosis, diabetic neuropathy, kidney disease including diabetic nephropathy, cardiovascular disease, stroke and diabetic retinopathy and arteriovascular disease.

"Biomarker" in the context of the present invention encompasses, without limitation, the proteins in Table 1 or 2 and de facto measures thereof; nucleic acids encoding the proteins in Table 1 or 2; metabolites and degradation products of the proteins in Table 1 or 2; polymorphisms, mutations, variants, modifications, subunits, peptides (such as those in Table 3) and fragments of the proteins in Table 1 or 2; and protein-ligand complexes including the proteins in Table 1 or 2. Biomarkers can also include proteins with at least 50%, 60%, 70%, 80%, 90%, 95%, 96%, 97%, 98% or 99% identity or similarity with the proteins in Table 1 or 2 as well as mutated forms of the proteins in Table 1 or 2 and nucleic acids encoding such mutations. The Biomarkers can be used to calculate mathematical indices or other measurements, including temporal trends and differences that are useful with respect to the present invention.

"Gestational Diabetes" refers to glucose intolerance during pregnancy. This condition results in high blood sugar that starts or is first diagnosed during pregnancy.

"Hypoglycaemic" agents include oral hypoglycaemic agents and include, without limitation, first-generation sulfonylureas: Acetohexamide, Chlorpropamide, Tolbutamide; second-generation sulfonylureas: Glipizide, Glyburide, Glimepiride; Biguanides: Metformin; Alpha-glucosidase inhibitors: Acarbose, Miglitol, Thiazolidinediones: Rosiglitazone, Pioglitazone, Troglitazone; Meglitinides: Repaglinide; and other hypoglycemics such as Acarbose; Buformin; Butoxamine Hydrochloride; Camiglibose; Ciglitazone; Englitazone Sodium; Darglitazone Sodium; Etoformin Hydrochloride; Gliamilide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat.

"Impaired fasting glucose" (IFG) is a pre-Diabetic condition associated with a blood glucose level that is higher than normal, but not high enough to be classified as Diabetes. A subject with IFG may have a fasting blood sugar (glucose) level below or equal to 125 mg/L, between 100 and 125 mg/dL or between 105 and 125 mg/dL.

The term "identity," used herein refers to a relationship between the sequences of two or more molecules, as determined by comparing the sequences. "Identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs.

"Impaired glucose tolerance" (IGT) is a pre-Diabetic condition associated with a blood glucose level that is higher than normal, but not high enough to be classified as Diabetes. A subject with IGT may have two-hour glucose levels of 140 to 199 mg/dL (7.8 to 11.0 mmol) on the 75-g oral glucose tolerance test.

"Lipid reducing agents" include gemfibrozil, cholystyramine, colestipol, nicotinic acid, and HMG-CoA reductase inhibitors such as simvastatin, lovastatin, pravastatin sodium, fluvastatin, atorvastatin and cerivastatin.

The term "measuring" and variants such as "measure" as used herein in relation to the biomarkers described herein refers to determining the presence and/or quantity of a given biomarker.

"pre-Diabetes" is a state in which some but not all of the diagnostic criteria for Diabetes are met. It includes conditions where subjects display blood sugar levels between normal and diabetic levels, conditions where subjects suffer from impaired glucose tolerance (IGT), impaired fasting glucose (IFG) and/or glycated haemoglobin between 5.7 and 6.4%.

A "sample" in the context of the present invention is a biological sample isolated from a subject and can include, by way of example and not limitation, whole blood, blood fraction, serum, plasma, blood cells, endothelial cells, tissue biopsies, lymphatic fluid, ascites fluid, interstitial fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids.

The term "similarity" is a related concept to "identity", but in contrast refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The term "conservative amino acid substitution" refers to a substitution of a native amino acid residue with a normative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine. General rules for conservative amino acid substitutions are set forth in the table hereunder:

| Original Residues | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala, Tyr | Leu |
| Pro | Ala | Ala |
| Ser | Thr | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties. Conservative modifications to the amino acid sequence (and the corresponding modifications to the encoding nucleotides) are expected to produce polypeptides having functional and chemical characteristics similar to those of the biomarkers in Table 1. In contrast, substantial modifications in the functional and/or chemical characteristics of the biomarkers in Table 1 may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Preferred methods to determine identity and/or similarity are designed to give the largest match between the sequences tested. Methods to determine identity and similarity are codified in publicly available computer programs. Preferred computer program methods to determine identity and similarity between two sequences include the GCG program package, including GAP (Devereux et al., Nuc. Acids Res. 12:387 (1984); Genetics Computer Group, University of Wisconsin, Madison, Wis.), BLASTP, BLASTN, and FASTA (Atschul et al., J. Mol. Biol. 215:403-10 (1990)). The BLAST X program is publicly available from the National Center for Biotechnology Information (NCBI) and other sources (Altschul et al., BLAST Manual (NCB NLM NIH, Bethesda, Md.); Altschul et al., 1990, supra). The well-known Smith Waterman algorithm may also be used to determine identity.

A "subject" in the context of the present invention is preferably a mammal. The mammal can be a human, non-human primate, mouse, rat, dog, cat, horse, or cow. A subject can be one who has been previously diagnosed or identified as having Diabetes, pre-Diabetes, or a Diabetes related condition, and optionally has already undergone, or is undergoing, a therapeutic intervention for the Diabetes, pre-Diabetes, or Diabetes related condition. Alternatively, a subject can also be one who has not been previously diagnosed as having pre-Diabetes, Diabetes and/or a Diabetes related condition. For example, a subject can be one who exhibits one or more risk factors for pre-Diabetes, Diabetes and/or a Diabetes related condition, or a subject who does not exhibit any such risk factors or a subject who is asymptomatic for pre-Diabetes, Diabetes and/or a Diabetes related condition. A subject can also be one who is suffering from or at risk of developing pre-Diabetes, Diabetes and/or a Diabetes related condition.

Diagnostics and Prognostics

The invention provides improved diagnosis and prognosis of pre-Diabetes, Diabetes or a Diabetes related condition. The risk of developing pre-Diabetes, Diabetes or a Diabetes related condition can be assessed by measuring one or more of the biomarkers described herein, and comparing the measured values to reference or index values. Such a comparison can be undertaken with mathematical algorithms or formula in order to combine information from results of multiple individual biomarkers and other parameters into a single measurement or index. Subjects identified as having an increased risk of pre-Diabetes, Diabetes or a Diabetes related condition can optionally be selected to receive treatment regimens, such as administration of prophylactic or therapeutic compounds or implementation of exercise regimens or dietary supplements to prevent, treat or delay the onset of pre-Diabetes, Diabetes or a Diabetes related condition.

The amount of the biomarker can be measured in a test sample and compared to a reference or normal level, utilizing techniques such as reference limits, discrimination limits, or risk defining thresholds to define cut-off points and abnormal values for pre-Diabetes, Diabetes or a Diabetes related condition. The normal control level is the level of one or more biomarkers or combined biomarker indices typically found in a subject not suffering from pre-Diabetes, Diabetes or a Diabetes related condition. The normal and abnormal levels and cut-off points may vary based on whether a biomarker is used alone or in a formula combining with other biomarkers into an index. Alternatively, the normal or abnormal level can be a database of biomarker patterns or "signatures" from previously tested subjects who did or did not develop or convert to pre-Diabetes, Diabetes or a Diabetes related condition over a clinically relevant time horizon.

The present invention may be used to make continuous or categorical measurements of the risk of develop or convert to pre-Diabetes, Diabetes or a Diabetes related condition, thus diagnosing and defining the risk spectrum of a category of subjects with a defined clinical status. In the categorical scenario, the methods of the present invention can be used to discriminate between normal cohorts and cohort with pre-Diabetes, Diabetes or a Diabetes related condition. In other embodiments, the present invention may be used so as to discriminate pre-Diabetes from Diabetes, Diabetes from normal, different Diabetes related conditions or different Diabetes conditions from normal. Such differing use may require different biomarker combinations in individual panels, mathematical algorithms, and/or cut-off points, but subject to the same aforementioned measurements of accuracy for the intended use.

Identifying a subject before they develop pre-Diabetes, Diabetes or a Diabetes related condition enables the selection and initiation of various therapeutic interventions or treatment regimens in order to delay, reduce or prevent that subject's conversion to a disease state. Monitoring the levels of at least one biomarker also allows for the course of treatment of pre-Diabetes, Diabetes or a Diabetes related condition to be monitored. For example, a sample can be provided from a subject undergoing treatment regimens or therapeutic interventions, e.g., drug treatments, for pre-Diabetes, Diabetes or a Diabetes related condition. Such treatment regimens or therapeutic interventions can include exercise regimens, dietary modification, dietary supplementation, bariatric surgical intervention, administration of pharmaceuticals, and treatment with therapeutics or prophylactics used in subjects diagnosed or identified with pre-Diabetes, Diabetes or a Diabetes related condition. Samples can be obtained from the subject at various time points before, during, or after treatment.

The present invention can also be used to screen populations in a variety of settings. For groups of subjects can be screened: to identify those requiring interventions; for the collection of epidemiological data; to assess them for health insurance purposes. Data obtained through population screens will be particularly valuable when correlated with clinical measures of pre-Diabetes, Diabetes or a Diabetes related condition and can be stored in data arrays or other collections in machine-readable media for convenient use by healthcare service providers and the allied health industry to improve service delivery and efficiency and hence improve patient outcomes.

A machine-readable storage medium includes any data storage material encoded with machine readable data or data arrays which, when using a machine programmed with instructions for using said data, is capable of use for a variety of purposes, such as, without limitation, providing or generating subject information relating to pre-Diabetes, Diabetes or a Diabetes related condition risk factors over time or in response to interventions or therapies and drug discovery. Assessment or measurement of the biomarkers of the invention and/or the corresponding risk determined therefrom may be implemented in computer programs executing on programmable computers, comprising, inter alia, a processor, a data storage system (including volatile and non-volatile memory and/or storage elements), at least one input device, and at least one output device. Program code or software can be applied to input data to perform the functions required to generate the required output.

The program code or software can perform one or more of the functions in relation to data concerning the biomarkers including: determining normal or abnormal levels of a biomarker and comparing a level of a biomarker to a reference value, e.g. a control subject or population whose pre-Diabetes, Diabetes or a Diabetes related condition state is known or an index value or baseline value. The reference sample or index value or baseline value may be taken or derived from one or more subjects who have been exposed to a treatment, or may be taken or derived from one or more subjects who are at low risk of developing pre-Diabetes, Diabetes or a Diabetes related condition, or may be taken or derived from subjects who have shown improvements in one or more risk factors associated with pre-Diabetes, Diabetes or a Diabetes related condition (including established clinical parameters) as a result of exposure to a treatment. The reference sample or index value or baseline value may also be taken or derived from one or more subjects who have not been exposed to the treatment. For example, samples may be collected from subjects who have received initial treatment for pre-Diabetes, Diabetes or a Diabetes related condition and subsequent treatment for pre-Diabetes, Diabetes or a Diabetes related condition to monitor the progress of the treatment. A reference value can also comprise a value derived from a risk prediction algorithm or computed indices from population studies.

The biomarkers of the present invention can thus be used to generate a biomarker profile or signature of subjects: (i) who do not have and are not expected to develop pre-Diabetes, Diabetes or a Diabetes related condition and/or (ii) who have or expected to develop pre-Diabetes, Diabetes or a Diabetes related condition. The biomarker profile of a subject can be compared to a predetermined or reference biomarker profile to diagnose or identify subjects at risk for developing pre-Diabetes, Diabetes or a Diabetes related condition, to monitor the progression of disease, as well as the rate of progression of disease, and to monitor the effectiveness of pre-Diabetes, Diabetes or a Diabetes related condition treatments. Biomarker profiles of the present invention are preferably contained in a machine-readable medium and are "live" insofar as they can be updated with further data that comes to hand, thus improving the strength and clinical significance of the biomarkers. Data concerning the biomarkers of the present invention can also be combined or correlated with other data or test results, such as, without limitation, measurements of clinical parameters or other algorithms for pre-Diabetes, Diabetes or a Diabetes related condition. Other data includes age, ethnicity, body mass index (BMI), total cholesterol levels, blood glucose levels, blood pressure, LDL and HDL levels. The machine-readable media can also comprise subject information such as medical history and any relevant family history.

The present invention also provides methods for identifying agents for treating pre-Diabetes, Diabetes or a Diabetes related condition that are appropriate or otherwise customised for a specific subject. In this regard, a test sample from a subject, exposed to a therapeutic agent or a drug, can be taken and the level of one or more biomarkers can be determined. The level of one or more biomarkers can be compared to a sample derived from the subject before and after treatment, or can be compared to samples derived from one or more subjects who have shown improvements in risk factors as a result of such treatment or exposure.

Tests

The biomarkers and panels thereof of the present invention can be implemented in a range of test systems. Typically, test systems include a means for obtaining test results from a sample, a means for collecting, storing, processing and/or tracking test results for the sample, usually in a database and a means for reporting test results. The means for obtaining test results can include a module adapted for automatic testing utilising one or more of biochemical, immunological and nucleic acid detection assays. Some test systems can process multiple samples and can run multiple tests on a given sample. The means for collecting, storing, processing and/or tracking test results may comprise a physical and/or electronic data storage device such as a hard drive or flash memory or paper print-outs. The means for reporting test results can include a visible display, a link to a data structure or database, or a printer. In this regard, the reporting means may simply be a data link that is adapted to send results to another device such as a database, visual display, or printer.

Thus, the present invention provides a test system adapted to aid in the identification of individuals at risk of developing pre-Diabetes, Diabetes or a Diabetes related condition or diagnose pre-Diabetes, Diabetes or a Diabetes related condition, the test system comprising a means that uses data relating to at least one of the biomarkers described herein. Typically, test results from system of the present invention serve as inputs to a computer or microprocessor programmed with a machine code or software that takes the data relating to at least one of the biomarkers described herein and determines the risk of developing or already having pre-Diabetes, Diabetes or a Diabetes related condition.

Biomarker Selection

The biomarkers in Table 1 have been identified as being found to have altered or modified presence or concentration levels in subjects who have Diabetes and or diabetic nephropathy. Thus, the biomarkers and methods of the present invention allow one of skill in the art to identify, diagnose, or otherwise assess subjects who do not exhibit any symptoms of pre-Diabetes, Diabetes or a Diabetes related condition, but who nonetheless may have or be at risk for developing pre-Diabetes, Diabetes or a Diabetes related condition.

One or more of the biomarkers in Table 1 or 2 can be selected to form a panel of markers. For example, one embodiment of the invention is a method of evaluating the risk of developing pre-Diabetes, Diabetes or a Diabetes related condition, comprising the step of measuring the levels of at least 2, 3, 4, 5, 6, 7, 8, 9, 10, 11, 12 or 13 biomarkers from Table 1 or 2. Preferably, the panel includes at least one of: Peroxiredoxin-2 (P32119), Protein AMBP (P02760); Apolipoprotein A-IV (P06727) and Complement C1q subcomponent subunit B (P02746); at least one of Adiponectin (Q15848), Complement factor H-related protein 2 (P36980), Haemoglobin subunit beta (P68871), Apolipoprotein B-100 (P04114) and Sulfhydryl oxidase 1 (O00391) or; at least one of Apolipoprotein C-III (P02656), Insulin-like growth factor-binding protein 3 (P17936), CD5 antigen-like (O43866) and Complement component C8 beta chain (P07358).

Clinical Algorithms

Results obtained using the biomarkers of the present invention can be combined into indices useful in the practice of the invention using any one or more formulae. As indicated above, and without limitation, such indices may indicate, among the various other indications, the probability, likelihood, absolute or relative risk, time to or rate of conversion from one to another disease states, or make predictions of future biomarkers measurements of pre-Diabetes, Diabetes or a Diabetes related condition. This may be for a specific time period or horizon, or for remaining lifetime risk, or simply be provided as an index relative to another reference subject population.

Preferred formulas include the broad class of statistical classification algorithms such as relative operating characteristic (ROC), the use of discriminant analysis e.g. linear discriminant analysis (LDA). Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic. Other formulas include a support vector machine (SVM), a random forest or recursive partitioning can also be used separately or in combination to identify biomarker combinations that are most important.

Other formula may be used in order to pre-process the results of individual biomarker measurements into more valuable forms of information, prior to further processing. Pre-processing includes inverse and square root transformations, normalisation of biomarker results, using mathematical transformations such as logarithmic or logistic functions. Normalisations based on clinical parameters such as age, gender, race, BMI or sex are particularly preferred.

One or more clinical parameters may be used in the practice of the invention in combination with the biomarkers of the present invention as an input to a formula or as pre-selection criteria defining a relevant population to be measured using a particular biomarker panel and formula. Clinical parameters may also be useful in the biomarker normalization and pre-processing, or in biomarker selection, panel construction, formula type selection and derivation, and formula result post-processing.

The biomarker panels of the present invention may be tailored to the population and end point or use that is intended. For example, biomarker panels and formulas may be used for assessment of subjects for primary prevention and diagnosis and for secondary prevention and management. For primary assessment, the panels and formulas may be used for prediction and risk stratification for conditions, for the diagnosis of diabetic conditions, for the prognosis of glucose level and rate of change and for indication for future diagnosis. For secondary prevention and management, the panels and formulas may be used for prognosis and risk stratification for Diabetes complications. The panels and formulas may be used for clinical decision support, such as determining whether to defer intervention to next visit, to recommend normal preventive check-ups, to recommend increased visit frequency, to recommend increased testing and to recommend therapeutic intervention. The panels and formulas may also be useful for intervention in subjects with diabetic conditions, such as therapeutic selection and response, adjustment and dosing of therapy, monitoring ongoing therapeutic efficiency and indication for change in therapeutic intervention.

The disease endpoints of the invention include pre-Diabetes, Diabetes or a Diabetes related condition. The panels and formulas herein may be used to evaluate current status of the disease endpoints by aiding in the diagnosis and/or the determination of severity of the pre-Diabetes, Diabetes or a Diabetes related condition and/or determination of the subclass of the disease or condition. The panels and formulas herein are also useful for determining the future status of intervention such as determining the prognosis of future pre-Diabetes, Diabetes or a Diabetes related condition with therapy, intervention and drug therapy. The invention may be tailored to a specific intervention, drug class, therapeutic class or therapy or drug therapy or a combination thereof.

The surrogate endpoints of the invention include measuring HBA1c, glucose (I7PG and OGTT), and glucose class (normal glucose tolerance (NGT), IGT, IFG and T2DM). The panels and formulas herein are useful for determining the current status of the surrogate endpoints by diagnosing glucose class with or without fasting. The future status of surrogate endpoints may be determined using the biomarker panels herein such as determination of the prognosis of future glucose class. The biomarker panels and formulas are also useful for determining the future status of intervention such as determination of prognosis of future glucose class with drug therapy.

The complication endpoints of diabetic conditions include the Diabetes related conditions herein such as kidney disease, eye retinopathy, microvascular damage, liver damage, limb amputation and cardiovascular complications. The biomarker panels and formulas may be used to evaluate the current status of the disease endpoints by aiding in the diagnosis of pre-Diabetes, Diabetes or a Diabetes related condition. The future status of complication endpoints may be determined using the biomarker panels and formulas such as determination of the prognosis of future pre-Diabetes, Diabetes or a Diabetes related condition. The panels and formulas are also useful for determining the future status of intervention such as determining the prognosis of future pre-Diabetes, Diabetes or a Diabetes related condition with therapy.

Agents for Treating or Reducing the Risk of Developing Pre-Diabetes, Diabetes or a Diabetes Related Condition The biomarkers of the present invention can also be used to identify and assess agents for treating or reducing the risk of developing pre-Diabetes, Diabetes or a Diabetes related condition. Thus, the present invention also provides a method of identifying or assessing an agent for treating or reducing the risk of developing pre-Diabetes, Diabetes and/or a Diabetes related condition comprising:

(i) contacting cells expressing at least one biomarker from Table 1 or 2 with a putative agent; and
(ii) comparing expression or level of at least one biomarker from Table 1 or 2 in the cells prior to contact with the putative agent to expression of at least one biomarker from Table 1 or 2 in the cells after contact with the putative agent;

wherein a change in expression or level identifies the agent as an agent for treating pre-Diabetes, Diabetes and/or a Diabetes related condition.

The cells may be contacted with the putative agent in vivo, such as in an animal model, or in vitro, such as in a cell culture or line. The expression or level may be compared using a computer driven program or software.

The present invention also provides a method of treating or reducing the risk of developing pre-Diabetes, Diabetes and/or a Diabetes related condition in a subject comprising administering an effective amount of an agent adapted to change the expression or level of at least one biomarker in Table 1 or 2 to the subject.

The agent may be administered according to any one of the known methods as selected by a suitably qualified practitioner. The agents may be administered as part of a composition comprising an effective amount of the agent in admixture with a pharmaceutically acceptable agent such as a pharmaceutically acceptable carrier. The carrier material may be water for injection, preferably supplemented with other materials common in solutions for administration to mammals. Standard pharmaceutically acceptable agents such as carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

The optimal formulation of the agent will be determined by one skilled in the art depending upon the intended route of administration, delivery format and desired dosage. See, e.g., Remington's Pharmaceutical Sciences, 1435-1712 (18th Ed., A. R. Gennaro, ed., Mack Publishing Company 1990). Such compositions may influence the physical state, stability, rate of in vivo release, and rate of in vivo clearance.

Thus, the present invention also provides for the use of an agent adapted to change the expression or level of at least one biomarker in Table 1 or 2 for preparing a medicament for treating or reducing the risk of developing pre-Diabetes, Diabetes and/or a Diabetes related condition.

Preferably the agent adapted to change the expression or level of at least one biomarker in Table 1 or 2 is an agent for treating or reducing the risk of developing pre-Diabetes, Diabetes and/or a Diabetes related condition as defined herein. Other Agents for treating or reducing the risk of developing pre-Diabetes, Diabetes and/or Diabetes related conditions include, lipase inhibitors such as cetilistat; synthetic amylin analogs such as Symlin pramlintide with or without recombinant leptin; sodium-glucose cotransporter 2 inhibitors like sergliflozin, YM543, dapagliflozin, dual adipose triglyceride lipase and PI3 kinase activators like Adyvia; antagonists of neuropeptide Y2, Y4, and Y5 receptors, synthetic analog of human hormones PYY3-36 and pancreatic polypeptide; cannabinoid CB1 receptor antagonists such as rimonabant, taranabant, CP-945,598, hormones like oleoyl-estrone; inhibitors of serotonin, dopamine, and norepinephrine (also known in the art as "triple monoamine reuptake inhibitors") like tesofensine; inhibitors of norepinephrine and dopamine reuptake, like Contrave (bupropion plus opioid antagonist naltrexone) and Excalia (bupropion plus anticonvulsant zonisaminde); inhibitors of 111.beta.-hydroxysteroid dehydrogenase type 1 (11b-HSD1); inhibitors of cortisol synthesis such as ketoconazole; inhibitors of gluconeogenesis; glucokinase activators; antisense inhibitors of protein tyrosine phosphatase-1B; as well as other agents like injections of gastrin and epidermal growth factor (EGF) analogs such as Islet Neogenesis Therapy (E1-I.N.T.); and betahistine.

Biomarker Measurement

Biomarkers may be measured using one or more of a range of techniques. Preferably the biomarkers are measured in a way that minimises subject variability. For example, they may be measured in a fasting state, and most commonly in the morning, providing a reduced level of subject variability due to both food consumption and metabolism and diurnal variation. Any fasting or temporal-based sampling procedure can be used in the present invention.

The actual measurement of levels of the biomarkers herein can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Biomarker levels can also be measured using reverse-transcription-based PCR assays (RT-PCR), e.g., using primers specific for the differentially expressed sequence of genes. Preferably, biomarker levels are determined at the protein level, e.g., by measuring the levels of peptides encoded by the gene products described herein, or activities thereof. Such methods include, e.g., immunoassays based on antibodies to proteins encoded by the genes, aptamers or molecular imprints.

The biomarkers in Table 1 or 2, polypeptides, peptides, mutations, and polymorphisms thereof can be detected in any suitable manner, but are typically detected by contacting a sample from the subject with an antibody which binds the biomarker protein, polypeptide, mutation, or polymorphism and then detecting the presence or absence of a reaction product. Antibodies can be monoclonal, polyclonal, chimeric, or a fragment of the foregoing, and the step of detecting the reaction product may be carried out with any suitable immunoassay.

Immunoassays carried out in accordance with the present invention may be homogeneous assays or heterogeneous assays. In a homogeneous assay the immunological reaction usually involves the specific antibody to the biomarker, a labelled analyte, and the sample of interest. The signal arising from the label is modified, directly or indirectly, upon the binding of the antibody to the labelled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include oligonucleotides, immunoblotting, immunoprecipitation, immunofluorescence methods, chemiluminescence methods, electrochemiluminescence (ECL) or enzyme-linked immunoassays.

Using sequence information provided by the database entries for the biomarkers in Table 1, expression of the biomarker sequences can be detected (if present) and measured using techniques well known to one of ordinary skill in the art such as Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA or RNA sequences in the test and reference cell populations.

Biomarker protein and/or nucleic acid metabolites can also be measured using one or more of a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry including multiple reaction monitoring (MRM) mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection.

When the biomarkers are measured using mass spectrometry they may be measured via a peptide selected from the list of:
  (i) a 5-25 amino acid peptide of a protein from Table 1 or 2;
  (ii) a 5-20 amino acid peptide of a protein from Table 1 or 2;
  (iii) a 10-20 amino acid peptide of a protein from Table 1 or 2;

(iv) a 10-15 amino acid peptide of a protein from Table 1 or 2; or (v) a peptide in Table 3.

Kits

The invention also includes a biomarker-detection reagent, e.g., an antibody specific for a biomarker protein in Table 1 or 2 or peptide in Table 3 or a nucleic acid that specifically identifies or binds to one or more nucleic acids encoding a biomarker protein in Table 1 or 2 or a peptide in Table 3 by having homologous nucleic acid sequences, such as oligonucleotide sequences or aptamers, complementary to a portion of the nucleic acid packaged together in the form of a kit. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions for carrying out the assay may also be included in the kit. The assay may for example be in the form of a Northern hybridization, sandwich ELISA or protein antibody array.

Reagents for detecting biomarkers of the present invention can be immobilized on a solid matrix such as a porous strip to form at least one biomarker detection site. The measurement or detection region of the porous strip may include a plurality of sites containing an antibody or nucleic acid. A test strip may also contain sites for negative and/or positive controls. Alternatively, control sites can be located on a separate strip from the test strip. Optionally, the different detection sites may contain different amounts of immobilized antibodies or nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences adapted to bind a nucleic acid sequence encoding a biomarker in Table 1 or 2. The substrate array can be on, e.g., a solid substrate or "chip". Alternatively, the substrate array can be a solution array.

EXAMPLES

Example 1

Identification and Validation of Diabetes Biomarkers

1. Materials/Methods
A. Cohort Description
A.1. Fremantle Diabetes Study (Phase 1)

Rational: The FDS1 cohort comprised 1294 patients who had type 2 diabetes. Diabetic subjects with and without diabetic nephropathy were selected to give markedly different phenotypic presentations enabling the greatest difference in protein expression.

The Fremantle Diabetes Study (FDS) Phase I was a longitudinal observational study of diabetes care, control, complications and cost in patients from a stable postcode-defined urban community of 120,097 people. When Phase I was conceived in 1991, there were few published diabetes natural history data.

| | |
|---|---|
| Study groups: | Adults type 2 diabetics, Anglo-Celts |
| Group 1: | Normoalbuminuria (ACR: 0.57-1.53 mg/mmol) |
| Group 2: | Macroalbuminuia (ACR: 49.0-300.0 mg/mmol) |
| Ages: | 33-84 years |
| Number of subjects: | 20 per group; 40 in total |
| Selection range: | 1294 |
| Protocol: | EDTA tube, centrifuged within 4 hours, separated & stored at −80° C. |
| Specimens: | Plasma, urine |

A.2. Fremantle Diabetes Study (Phase 2)

Rational: The FDS2 cohort recruited diabetics referred by clinicians in the Fremantle locality and those from the FDS1 cohort database. Diabetic subjects with and without diabetic nephropathy were selected to give markedly different phenotypic presentations enabling the greatest difference in protein expression.

Phase II was conceived in 2007 for improved and extended data collection in order to characterise the nature of diabetes in contemporary urban Australia.

| | |
|---|---|
| Study groups: | All adults type 2 diabetics, undifferentiated for race |
| Group 1: | Normoalbuminuria (ACR; 0.3-2.3 mg/mmol) |
| Group 2: | Macroalbuminuia (ACR 34.1-405.0 mg/mmol) |
| Group 3: | Microalbuminuria (ACR 3.5-18.3 mg/mmol) |
| Ages: | 44-85 years |
| Consent for genetics: | blood collected and stored |
| Number of subjects: | 20 per group; 60 in total |
| Selection range: | 2000 |
| Recruited from: | Fremantle Diabetes Study Phase 13 (680) + new recruits in Fremantle area |
| Protocol: | Proteomics International standard protocol |
| Specimens: | Plasma, serum, whole blood & urine |

A.3. Busselton Diabetes Study

Rational: Expand information on diabetic patients from a rural community. Complement information obtained from the FDS1 & FDS2 urban studies. Includes matched non-diabetic control subjects.

The Busselton Health Study is one of the longest running epidemiological research programs in the world. The residents of the town of Busselton, a coastal community in the south-west of Western Australia, have been involved in a series of health surveys since 1966. To date over 16,000 men, women & children of all ages have taken part in the surveys and have helped contribute to the understanding of many common diseases and health conditions.

| | |
|---|---|
| Study groups: | All adults with/without diabetes, undifferentiated for race, not age-matched |
| Group 1: | Diabetic with worst albuminuria (ACR 17.5-408 mg/mmol) |
| Group 2: | Diabetic with normoalbuminuria (ACR 0.4-2.6 mg/mmol) |
| Group 3: | Controls with normoalbuminuria (ACR 0.2-1.7 mg/mmol) |
| Ages: | 41-94 years |
| Consent for genetics: | blood collected and stored |
| Number of subjects: | 20 per group; 60 in total |
| Selection range: | 250 from 329 adults with diabetes, 250 controls from 2595 non-diabetic |
| Recruited from: | Busselton Health Survey |
| Protocol: | Proteomics International standard protocol |
| Specimens: | Plasma, serum, whole blood & urine |

B. Protein Biomarker Discovery Using iTRAQ and 2D LC MALDI TOF/TOF

This discovery methodology involves chemically labelling the plasma of different groups of patients (e.g. diabetic nephropathy vs. diabetic with no nephropathy) and determining by mass spectrometry the relative ratio of the presence of a particular protein. Proteins with significantly altered concentrations after analysis indicate a change in the biochemistry of one group of patients versus another. This technique was used to measure the relative concentrations of 130-200 proteins per sample. Proteins of significantly different concentration between groups were identified, and these were selected for further examination by MRM methodology (section C below).

B.1. Sample Preparation

Plasma samples (N=10 or 20) were pooled before immunodepletion of the 14 most abundant proteins using a MARS 14 HPLC column (Agilent Technologies). Immunodepleted samples were buffer exchanged using 10 kDa cut-off spin filters (Sartorius) into 1M Triethylammonium bicarbonate. The protein samples were reduced, alkylated, trypsin digested and labelled according to the iTRAQ protocol (Applied Biosystems).

B.2. Instrumental Analysis

Peptides were desalted on a Strata-X 33 μM polymeric reversed phase column (Phenomenex) before separation by strong cation exchange liquid chromatography (SCX) on an Agilent 1100 HPLC using a PolySulfoethyl column (4.6×100 mm, 5 μm, 300 Å). Peptides were eluted with a linear gradient of 0-400 mM KCl. SCX fractions were desalted and loaded onto an Ultimate 3000 nano HPLC system (Dionex C18, PepMap 100, 3 μm) and separated with a gradient of 10-40% acetonitrile (0.1% formic acid) with spotting using a ProBot (LC Packings) robotic spotter. The resultant spots were analysed on a 4800 MALDI TOF/TOF Analyzer.

B.3. Data Analysis

Data analysis was performed using ProteinPilot™ 2.0.1 software (Applied Biosystems). False discovery rates were calculated using the PSPEP algorithm that works in conjunction with ProteinPilot™ 2.0.1 and only proteins with a global false discovery rate (FDR) from fit of <5% were accepted.

C. Biomarker Candidate Validation Using Multiple Reaction Monitoring (MRM)

Multiple Reaction Monitoring (MRM) is a mass spectrometry-based approach to specifically target transitions (precursor-fragment ion pairs) for a signature peptide, which represents a surrogate for the whole biomarker candidate protein. For each candidate one or two peptides unique to that protein (when compared to the SwissProt Human Database ver 57.1) were used. This high-throughput approach was used to validate biomarkers from the discovery phase (see Section B above) in a larger number of individual patient plasma samples.

C.1. Sample Preparation

Pooled samples identical to previous iTRAQ experiments as well as individual samples (N=10 per group) different from previous iTRAQ pools (validation samples) were prepared. Samples were immunodepleted of the 14 most abundant proteins using a MARS 14 HPLC column. Immunodepleted samples were buffer exchanged using 10 kDa cut-off spin filters. The protein samples were reduced, alkylated, trypsin digested and desalted. In addition, one plasma reference sample (pool of healthy individuals) was $^{18}O$ labelled and finally spiked into each cohort sample (1:1) prior to LC-MRM/MS analysis.

C.2. Translating Biomarker Lists into MRM Transition Lists

Preliminary MRM transition lists were generated by a series of steps which included downloading protein sequences, digesting proteins in silico in conjunction with a filter (e.g. 7-21 amino acids, 0 missed cleavage) and selecting a minimum of 4 transitions per peptide (usually precursor charge z2, product charge z1). Useful information on proteotypic peptides from literature and repositories (PeptideAtlas, MRMaid) was also incorporated and the selection of transitions was supported by spectral libraries (ISB, NIST, GPM, BiblioSpec). An open-source software called Skyline (MacCoss laboratory, University of Washington, Seattle, Wash., USA) was used to generate and refine MRM transitions as well as to analyse MRM transition data.

An aliquot of 1 ug of plasma digest was directly loaded onto a nano column (Dionex C18, PepMap 100, 3 μm) and peptides were eluted with a 100 min gradient of 2-30% acetonitrile (0.1% formic acid) into a 4000 QTrap equipped with a nanoelectrospray ionisation source. A maximum of 200 MRMs were acquired per run with a dwell time of 20 ms and a cycle of 5 s. Runs were analysed (i.e. peptides without reasonable transitions were deleted) and a refined list of peptides and transitions was subjected to an MRM triggered MS/MS experiment to validate peptide assignment. Since peptide assignment for low abundant proteins is a quite challenging task without standards, product ion scan (EPI) settings varied e.g. scan rate (1000-4000), LIT fill time (20-300 ms). The two most intense transitions per peptide were selected for validation and were sent for MS/MS (mass range 200-1200) when a transition exceeded a threshold of 1000 cps. In total 40 MRMs per run were used with a dwell time of 20 ms and a cycle of ~7 s. Acquired MS/MS data were searched against a current SwissProt database with human taxonomy filter using MASCOT. Peptides identified were matched against MRM data (peptide sequence, retention time). Finally, validated peptides were tested for their suitability to be used with the MRM $^{18}O$ labelling method. The final transition list for each cohort study consisted of 1-2 peptides (see Table 3) per candidate protein (see Table 1) and 3 transitions per peptide. If possible, peptide sequences which were not unique to the candidate protein and peptides with amino acids M, W, N-terminal Q or E, etc. were excluded.

TABLE 3

| Protein name (see Table 1) | Accession number (Uniprot) | Position/Peptide sequences (SEQ ID NO) | Key |
|---|---|---|---|
| Sulfhydryl oxidase 1 | sp\|O00391\|QSOX1_HUMAN | 257-265 SFYTAYLQR (SEQ ID NO: 1) | L |
| Apolipoprotein A-IV | sp\|P06727\|APOA4_HUMAN | 135-143 LEPYADQLR (SEQ ID NO: 2) | APOA4/LEP |
|  | sp\|P06727\|APOA4_HUMAN | 256-264 ISASAEELR (SEQ ID NO: 3) | APOA4/ISA |
| CD5 antigen-like | sp\|O43866\|CD5L_HUMAN | 246-256 LVGGDNLCSGR (SEQ ID NO: 4) | CD5L/LVG |
|  | sp\|O43866\|CD5L_HUMAN | 308-314 IWLDNVR (SEQ ID NO: 5) | CD5L/IWL |

TABLE 3-continued

| Protein name (see Table 1) | Accession number (Uniprot) | Position/Peptide sequences (SEQ ID NO) | Key |
|---|---|---|---|
| Complement component C8 beta chain | sp\|P07358\|CO8B_HUMAN | 122-132 CEGFVCAQTGR (SEQ ID NO: 6) | M |
| Apolipoprotein B-100 | sp\|P04114\|APOB_HUMAN | 642-654 SVSLPSLDPASAK (SEQ ID NO: 7) | APOB/SVS |
|  | sp\|P04114\|APOB_HUMAN | 950-960 TEVIPPLIENR (SEQ ID NO: 8) | APOB/TEV |
| Peroxiredoxin-2 | sp\|P32119\|PRDX2_HUMAN | 17-26 ATAVVDGAFK (SEQ ID NO: 9) | PRDX2/ATA |
| Protein AMBP | sp\|P02760\|AMBP_HUMAN | 283-293 TVAACNLPIVR (SEQ ID NO: 10) | AMBP/TVA |
|  | sp\|P02760\|AMBP_HUMAN | 335-349 EYCGVPGDGDEELLR (SEQ ID NO: 11) | AMBP/EYC |
| Hemoglobin subunit beta | sp\|P68871\|HBB_HUMAN | 10-18 SAVTALWGK (SEQ ID NO: 12) | I1 |
|  | sp\|P68871\|HBB_HUMAN | 19-31 VNVDEVGGEALGR (SEQ ID NO: 13) | I2 |
| Complement C1q subcomponent subunit B | sp\|P02746\|C1QB_HUMAN | 122-128 IAFSATR (SEQ ID NO: 14) | C1QB/IAF |
| Apolipoprotein C-III | sp\|P02656\|APOC3_HUMAN | 45-60 DALSSVQESQVAQQAR (SEQ ID NO: 15) | APOC3/DAL |
| Insulin-like growth factor-binding protein 3 | sp\|P17936\|IBP3_HUMAN | 47-63 ALAQCAPPPAVCAELVR (SEQ ID NO: 16) | IBP3/ALA |
|  | sp\|P17936\|IBP3_HUMAN | 226-233 FLNVLSPR (SEQ ID NO: 17) | IBP3/FLN |
| Adiponectin | sp\|Q15848\|ADIPO_HUMAN | 78-92 GDIGETGVPGAEGPR (SEQ ID NO: 18) | ADIPO/GDI |
| Complement factor H-related protein 2 | sp\|P36980\|FHR2_HUMAN | 233-242 TGDIVEFVCK (SEQ ID NO: 19) | FHR2/TGD |
|  | sp\|P36980\|FHR2_HUMAN | 262-270 LVYPSCEEK (SEQ ID NO: 20) | FHR2/LVY |

C.3. Instrumental Analysis

All samples were reconstituted and spiked 1:1 with an $^{18}O$ labelled reference plasma (pool of healthy individuals) prior to LC-MRM/MS analysis to correct for spray efficiency and ionization differences between runs. Each sample was injected in duplicate directly onto a nano column (Dionex C18, PepMap 100, 3 μm) and peptides were eluted in a 100 min gradient of 2-30% acetonitrile (0.1% formic acid) into a 4000 QTrap equipped with a nanoelectrospray ionisation source. The scheduled MRM option was used for all data acquisition with a target scan time of 4 s (at least 8 data points across a peak) and a 6-8 min MRM detection window which resulted in minimum dwell times of 50-60 ms.

C.4. Data Analysis

All transitions were integrated and for each peptide a (weighted) ratio of area of unlabelled peptide to area of labelled peptide was calculated. Ratios were normalised for population-based differences based on an invariate set of proteins. Finally, a Mann-Whitney test for non-parametric data was applied to the normalised ratios and a p value was calculated, which defines a protein as significantly differentially expressed between two subject groups, e.g. healthy vs. diseased.

The sensitivity, or true positive rate, vs. false positive rate (Relative Operating Characteristic curves) were also plotted for a range of markers (univariate and multivariate). A number of statistical transformations were used to improve power including natural logarithm (ln), inverse (inv) and square root (√).

2. Results

D. Biomarkers

D1. Biomarkers for Diabetic Nephropathy in Diabetic Patients

The table in FIG. 1 shows biomarker protein data from the Busselton and both Fremantle Diabetes Studies with respect to the presence of diabetic nephropathy where all subjects had diabetes. The question that is addressed is 'What are the biomarkers for diabetic nephropathy in diabetic patients?'

Figure 3:
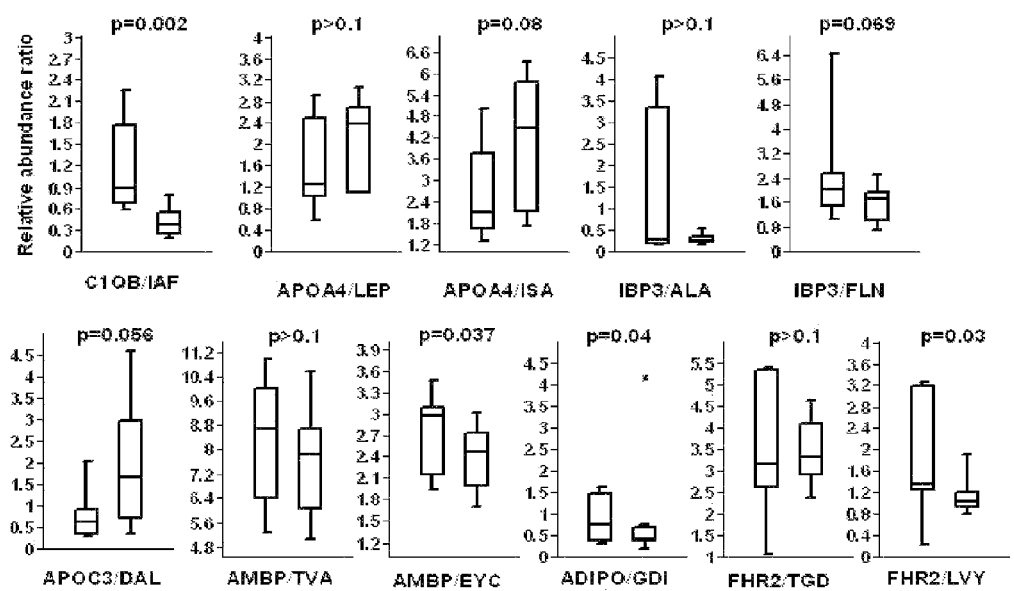
FIG. 3 is a series of box-whisker plots for each biomarker listed in FIG. 1 from the FDS2 study (left boxplot: diabetic group; right boxplot: diabetic group with severe nephropathy; x-axis: protein/peptide; y-axis: Relative abundance ratio; peptide sequences: IAF=IAFSATR; LEP=LEPYADQLR; ISA=ISASAEELR; ALA=ALAQCAPPPAVCAELVR; and FLN=FLNVLSPR; DAL=DALSSVQESQVAQQAR; TVA=TVAACNLPIVR; EYC=EYCGVPGDGDEELLR; GDI=GDIGETGVPGAEGPR; TGD=TGDIVEFVCK; LVY=LVYPSCEEK)
Figure 4:
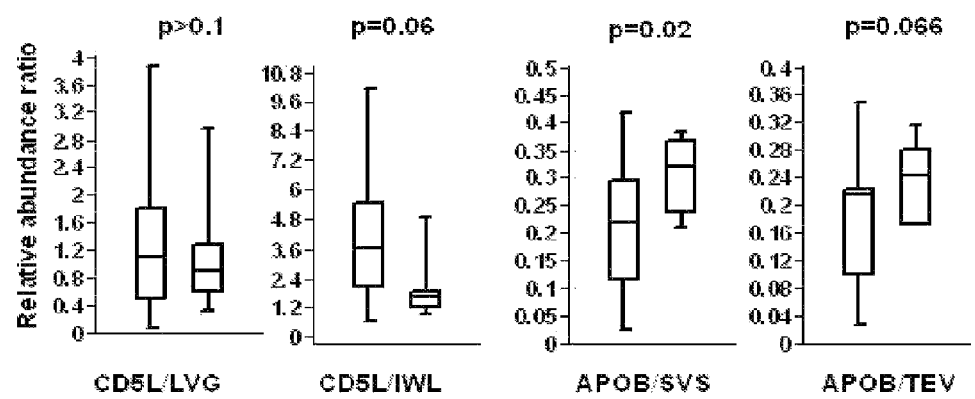
FIG. 4 is a series of box-whisker plots for each biomarker listed in FIG. 1 from the BDS study (left boxplot: diabetic group; right boxplot: diabetic group with severe nephropathy; x-axis: protein/peptide; y-axis: Relative abundance ratio; peptide sequences: LVG=LVGGDNLCSGR; IWL=IWLDNVR; SVS=SVSLPSLDPASAK; and TEV=TEVIPPLIENR)

The results of the table in FIG. 1 are illustrated as box-whisker plots in FIG. 2 (Study FDS1), FIG. 3 (Study FDS2) and FIG. 4 (Study BDS). For each biomarker candidate one to two signature peptides per protein were measured by MRM. (left boxplot: diabetic group; right boxplot: diabetic group with severe nephropathy; x-axis: protein/peptide; y-axis: Relative abundance ratio).

The ROC data in Tables 4-8 further illustrate that the biomarker(s) can be used as a diagnostic for diabetic nephropathy.

TABLE 4

Univariate analysis

| Peptide (Key-see Table 3) | Odds Ratio | Sensitivity | specificity | P | ROC AUC | Mean control | case | n |
|---|---|---|---|---|---|---|---|---|
| PRDX2/ATA (ln) | 17.7 | 80.0 | 80.0 | 0.040 | 0.860 | 0.245 | 0.507 | 20 |
| AMBP/TVA | 22.6 | 70.0 | 70.0 | 0.034 | 0.840 | 2.00 | 2.63 | 20 |
| AMBP/EYC | 1.42 | 60.0 | 80.0 | 0.061 | 0.850 | 10.6 | 14.1 | 20 |
| C1QB/IAF (ln) | 0.002 | 90.0 | 87.5 | 0.088 | 0.950 | 1.08 | 0.363 | 18 |

TABLE 5

Multivariate analysis (Model 3)

| Peptide (Key-see Table 3) | Odds Ratio | Sensitivity | specificity | P | ROC AUC | Mean control | case | n |
|---|---|---|---|---|---|---|---|---|
| PRDX2/ATA (ln) | 6.06 | 90.0 | 87.5 | 0.678 | 0.9625 | 0.265 | 0.61 | 18 |
| AMBP/TVA | 0.109 | | | 0.697 | | 2.04 | 2.68 | |
| AMBP/EYC | 2.10 | | | 0.426 | | 11 | 14.3 | |
| C1QB/IAF (ln) | 0.0004 | | | 0.287 | | 1.2 | 0.41 | |

TABLE 6

Multivariate analysis (Model FDS1)

| Peptide (Key-see Table 3) | Odds Ratio | Sensitivity | specificity | P | ROC AUC | Mean control | case | n |
|---|---|---|---|---|---|---|---|---|
| PRDX2/ATA (ln) | 6.52 | 90 | 90 | 0.254 | 0.89 | −1.41 | −0.68 | 20 |
| AMBP/TVA | 6.61 | | | 0.355 | | 2.04 | 2.67 | |
| AMBP/EYC | 1.01 | | | 0.97 | | 10.98 | 14.34 | |

TABLE 7

Multivariate analysis (Model FDS2)

| Peptide (Key-see Table 3) | Odds Ratio | Sensitivity | Specificity | P | ROC AUC | Mean control | Case | n |
|---|---|---|---|---|---|---|---|---|
| C1QB/IAF (ln) | 0.016 | 88.9 | 100 | 0.167 | 0.958 | 1.08 | 0.363 | 17 |
| AMBP/EYC | 0.044 | | | 0.218 | | 2.78 | 2.28 | |
| ADIPO/GDI (ln) | 0.281 | | | 0.589 | | 0.797 | 0.394 | |
| FHR2/LVY (√) | 0.342 | | | 0.842 | | 1.46 | 1.08 | |

TABLE 8

Multivariate analysis (Model BDS)

| Peptide (Key-see Table 3) | Odds Ratio | Sensitivity | Specificity | P | ROC AUC | Mean control | Case | n |
|---|---|---|---|---|---|---|---|---|
| CD5L/LVG (√) | 34679 | 66.7 | 80 | 0.209 | 0.922 | 0.796 | 0.890 | 19 |
| CD5L/IWL (ln) | 0.0009 | | | 0.151 | | 3.11 | 1.65 | |
| APOB/SVS | $5.42e^{25}$ | | | 0.076 | | 0.146 | 0.308 | |
| APOB/TEV | $1.95e^{-40}$ | | | 0.092 | | 0.130 | 0.237 | |

D2. Biomarkers for Diabetics with Nephropathy Versus Healthy Patients

The table in FIG. 5 describes the biomarkers discovered for patients with diabetic nephropathy versus a healthy control group without diabetes. This data is derived from the Busselton study.

As would be apparent, various alterations and equivalent forms may be provided without departing from the spirit and scope of the present invention. This includes modifications within the scope of the appended claims along with all modifications, alternative constructions and equivalents.

In the present specification, the presence of particular features does not preclude the existence of further features. The words "comprising", "including" and "having" are to be construed in an inclusive rather than an exclusive sense.

The invention claimed is:

1. A method of assessing a subject for diabetic nephropathy comprising measuring the concentration of at least one biomarker in a sample from the subject, wherein said at least one biomarker is CD5 antigen like, and based on the measured concentration:
   (i) designating the subject as having diabetic nephropathy where the measured concentration is consistent with concentrations of the at least one biomarker in samples from subjects who have diabetic nephropathy;
   (ii) designating the subject as having an increased risk of developing diabetic nephropathy where the measured concentration is consistent with concentrations of the at least one biomarker in samples from subjects who have an increased risk of developing diabetic nephropathy; or
   (iii) designating the subject as not having diabetic nephropathy or an increased risk of developing diabetic nephropathy where the measured concentration is consistent with concentrations of the at least one biomarker in samples from subjects who do not have diabetic nephropathy or an increased risk of developing diabetic nephropathy.

2. The method according to claim 1, wherein the at least one biomarker further comprises a biomarker selected from the group consisting of peroxiredoxin-2, protein AMBP, complement C1q subcomponent subunit B, apolipoprotein C-III, insulin-like growth factor-binding protein 3, adiponectin, complement factor H-related protein 2, apolipoprotein B-100, sulfhydryl oxidase 1, complement component C8 beta, and apolipoprotein A-IV.

3. The method according to claim 1, wherein the at least one biomarker further comprises a biomarker selected from the group consisting of apolipoprotein A-IV, insulin-like growth factor-binding protein 3.

4. The method according to claim 1, wherein the at least one biomarker further comprises apolipoprotein A-IV and insulin like growth factor binding protein 3.

5. The method according to claim 1, wherein the step of measuring the concentration of the at least one biomarker in a sample from the subject comprises measuring the concentration of a peptide fragment of the at least one biomarker.

6. The method according to claim 5, wherein the peptide fragment is a 5-25 amino acid peptide fragment.

7. The method according to claim 5, wherein the peptide fragment is selected from the group consisting of:
   SEQ ID NO: 1, Sulthydryl oxidase 1, 257-265, SFYTAYLQR;
   SEQ ID NO: 2, apolipoprotein A-IV, 135-143, LEPYADQLR;
   SEQ ID NO: 3, apolipoprotein A-IV, 256-264, ISASAEELR;
   SEQ ID NO: 4, CD5 antigen-like, 246-256, LVGGDNLCSGR;
   SEQ ID NO: 5, CD5 antigen-like, 308-314, IWLDNVR;
   SEQ ID NO: 6, complement component C8 beta chain, 122-132 CEGFVCAQTGR;
   SEQ ID NO: 7, apolipoprotein B-100, 642-654, SVSLPSLDPASAK;
   SEQ ID NO: 8, apolipoprotein B-100, 950-960, TEVIPPLIENR;
   SEQ ID NO: 9, peroxiredoxin-2, 17-26, ATAVVDGAFK;
   SEQ ID NO: 10, Protein AMBP, 283-293, TVAACNLPIVR;
   SEQ ID NO: 11, Protein AMBP, 335-349, EYCGVPGDGDEELLR;
   SEQ ID NO: 12, hemoglobin subunit beta, 10-18, SAVTALWGK;
   SEQ ID NO: 13, hemoglobin subunit beta, 19-31 VNVDEVGGEALGR;
   SEQ ID NO: 14, complement C1q subcomponent subunit B, 122-128 IAFSATR;
   SEQ ID NO: 15, apolipoprotein GM, 45-60, DALSSVQESQVAQQAR;
   SEQ ID NO: 16, insulin-like growth factor-binding protein 3, 47-63, ALAQCAPPPAVCAELVR;
   SEQ ID NO: 17, insulin-like growth factor-binding protein 3, 226-233 FLNVLSPR;
   SEQ ID NO: 18, adiponectin, 78-92, GDIGETGVPGAEGPR;
   SEQ ID NO: 19, complement factor H-related protein 2, 233-242, TGDIVEFVCK; and
   SEQ ID NO: 20, complement factor H-related protein 2, 262-270 LVYPSCEEK.

8. The method according to claim 5, wherein the peptide fragment is selected from the group consisting of:
   SEQ ID NO: 2, apolipoprotein A-IV, 135-143, LEPYADQLR;
   SEQ ID NO: 3, apolipoprotein A-IV, 256-264, ISASAEELR;
   SEQ ID NO: 4, CD5 antigen-like, 246-256, LVGGDNLCSGR;
   SEQ ID NO: 5, CD5 antigen-like, 308-314, IWLDNVR;
   SEQ ID NO: 16, insulin-like growth factor-binding protein 3, 47-63, ALAQCAPPPAVCAELVR; and SEQ ID NO: 17, insulin-like growth factor-binding protein 3, 226-233 FLNVLSPR.

9. The method according to claim 1, wherein the subject is asymptomatic for or only exhibits non-specific indicators of diabetic nephropathy.

10. The method according to claim 1, wherein the subject has been diagnosed with diabetic nephropathy.

11. The method according to claim 1, wherein the subject has kidney disease.

12. The method according to claim 1, wherein the subject has microalbuminuria, macroalbuminuria, or end stage renal disease.

13. The method according to claim 1, wherein the sample comprises a blood sample.

14. The method according to claim 5, wherein the peptide fragment is detected using mass spectrometry.

15. The method according to claim 1, wherein the subject has diabetes.

* * * * *